United States Patent [19]

Pitchen et al.

[11] Patent Number: 5,688,954

[45] Date of Patent: Nov. 18, 1997

[54] PROCESS FOR THE PREPARATION OF SUBSTITUTED THIOPYRAN-1-OXIDES

[75] Inventors: Philippe Pitchen, Dagenham, United Kingdom; Matthew Powers, Barto, Pa.; Patrick Leon, Tassin La Demi Lune; Dominique Petre, Lyons, both of France

[73] Assignee: Rhone-Poulenc Rorer Limited, Dagenham, United Kingdom

[21] Appl. No.: 633,749

[22] PCT Filed: Oct. 24, 1994

[86] PCT No.: PCT/GB94/02332

§ 371 Date: Apr. 24, 1996

§ 102(e) Date: Apr. 24, 1996

[87] PCT Pub. No.: WO95/11900

PCT Pub. Date: May 4, 1995

[30] Foreign Application Priority Data

Oct. 25, 1993 [GB] United Kingdom .................. 9321939

[51] Int. Cl.⁶ .................................................. C07D 409/04
[52] U.S. Cl. ......................... 546/268; 546/341; 435/118; 435/122
[58] Field of Search .......................... 546/268, 341; 435/118, 122

[56] References Cited

U.S. PATENT DOCUMENTS 5,120,852 6/1992 Aloup et al. ........................ 546/268

*Primary Examiner*—C. Warren Ivy
*Assistant Examiner*—Lyman H. Smith
*Attorney, Agent, or Firm*—Raymond S. Parker, III; Paul R. Darkes; Martin F. Savitzky

[57] ABSTRACT

A process is described for the preparation of a compound of formula (IX) from 4-hydroxybutyl 3-pyridyl ketone. The compound of formula (IX) is an intermediate useful in the preparation of (1R,2R)-2-(3-pyridyl)-N-alkyl-tetrahydro-2H-thiopyran-2-carbothioamide 1-oxides which possess useful pharmaceutical properties, for example anti-hypertensive properties.

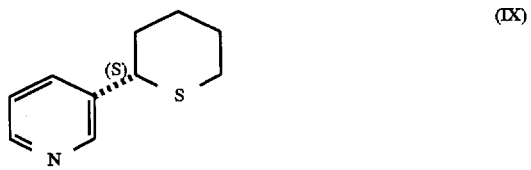

(IX)

11 Claims, No Drawings

PROCESS FOR THE PREPARATION OF SUBSTITUTED THIOPYRAN-1-OXIDES

This application is a 35 USC 371 National Stage filing of PCT/G894/02332 published as WO95/11900 on May 4, 1995.

This invention relates to a process for the preparation of intermediates useful in the preparation of (1R,2R)-2-(3-pyridyl)-N-alkyl-tetrahydro-2H-thiopyran-2-carbothioamide 1-oxides, which possess useful pharmaceutical properties, for example anti-hypertensive properties, and to intermediates and pharmaceutical products prepared using said process.

In the specifications of European Patent No. 0097584 and its equivalent U.S. Pat. No. 4,568,682 there are described compounds of general formula I, hereinafter depicted, wherein R represents a hydrogen atom or an alkyl group containing 1 to 4 carbon atoms, Het represents an aromatic heterocyclic radical and Y represents a bond or a methylene linkage.

The presence of two asymmetric centres leads to 4 diastereoisomers which may be separated into two racemic pairs of enantiomers which can be designated as "form A" (or the more polar product) and "form B" (or the less polar product), the relative polarity being determined by thin layer chromatography. Each of these two forms may be resolved, into its two enantiomers.

Among the compounds of formula I, form A of 2-(3-pyridyl)-N-methyltetrahydro-2H-thiopyran-2-carbothioamide 1-oxide consists of a mixture of trans-isomers which may be represented by formulae II and III, hereinafter depicted.

Studies carried out on isomers II and III have shown that the more active form is isomer III, whose absolute configuration is 1R,2R.

In the specifications of European Patent Application Publication No. 0426557 and its equivalent U.S. Pat. No. 5,120,852 there is described a process for the preparation of compounds of general formula IV, hereinafter depicted, wherein $R^1$ represents a straight- or branched-chain alkyl group containing 1 to 4 carbon atoms by the action of an alkyl isothiocyanate of the general formula:

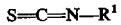

$$S=C=N-R^1 \qquad V$$

wherein $R^1$ is as hereinbefore defined, on the anion derived from a sulphoxide of formula VI or VII, hereinafter depicted, or on the anions derived from mixtures thereof.

According to the specifications of the aforementioned European Patent Application Publication No. 0426557 and U.S. Pat. No. 5,120,852, the compounds of formulae VI and VII may be prepared by the selective oxidation, by chemical or biochemical means, of the compounds of formula VIII, hereinafter depicted, which generally occur in the racemic form.

(1R,2S)-2-(3-pyridyl)tetrahydro-2H-thiopyran 1-oxide of formula VII is prepared by the diastereoselective oxidation of (S)-2-(3-pyridyl)tetrahydro-2H-thiopyran of formula IX, hereinafter depicted, which, according to a first feature of the present invention, is prepared by the cyclisation of compounds of the general formula XII hereinafter depicted, wherein $R^2$ represents a straight or branched $C_{1-4}$ alkyl group, preferably methyl and $R^3$ represents an alkyl-or arylsulphonyl group, eg a methanesulphonyl group, which, according to a further feature of the present invention, are prepared from compounds of formula X, which, according to another feature of the present invention are prepared by the stereoselective reduction, by chemical or biochemical means, of compounds of general formula XI, hereinafter depicted, wherein $R^2$ is as hereinbefore defined, or a salt or an addition compound thereof.

The preparation of (1R,2S)-2-(3-pyridyl)-tetrahydro-2H-thiopyran 1-oxide of formula VII, by the oxidation of (S)-2-(3-pyridyl)-tetrahydro-2H-thiopyran of formula IX, is carried out, for example, by means of a hypochlorite, such as sodium hypochlorite or by means of an organic hydroperoxide, e.g. peracetic acid or alpha,alpha-dimethylbenzyl hydroperoxide, or, more especially, by means of hydrogen peroxide, preferably in the presence of a catalyst such as a metal, for example zinc or a transition metal, e.g. cobalt, molybdenum, iron, vanadium or titanium or, more especially, copper, or a compound thereof, for example an acetylacetonate thereof.

The enantiomeric purity, i.e. the enantiomeric excess, of the (1R,2S)-2-(3-pyridyl)tetrahydro-2H-thiopyran 1-oxide of formula VII can be enhanced to values approaching 100% by recrystallisation from suitable solvent systems, for example ethyl acetate, toluene, methyl ethyl ketone, mixtures of methyl ethyl ketone with tert-butyl methyl ether, and mixtures of methyl ethyl ketone with acetone.

The preparation of compounds of formula XII, hereinafter depicted, wherein $R^2$ and $R^3$ are as hereinbefore defined may be carried out by treating a compound of formula X with an alkylsulphonyl or arylsulphonyl halide, preferably in the presence of a base such as a tertiary amine, e.g. triethylamine or pyridine. The subsequent cyclisation may be effected by treatment with a nucleophilic base such as an alkali metal alkoxide in an alkanol solvent, e.g. sodium methoxide in methanol or sodium ethoxide in ethanol. Preferably the reactions are carried out under an inert atmosphere.

The compounds of general formula XII wherein $R^2$ and $R^3$ are as hereinbefore defined and salts thereof are new compounds and they and the process for their preparation are further features of the present invention.

As will be appreciated by those skilled in the art, (R)-2-(3-pyridyl)tetrahydro-2H-thiopyran can be prepared in a similar manner but using, instead of a compound of formula X, the (S)-enantiomer thereof.

The compounds of general formula X wherein $R^2$ is as hereinbefore defined and salts thereof are also new compounds and are a further feature of the present invention.

They are prepared, according to another feature of the invention, by the stereoselective reduction, by chemical or biochemical means, of compounds of general formula XI, hereinafter depicted, wherein $R^2$ is as hereinbefore defined, or a salt thereof, for example an arylsulphonate or an alkylsulphonate, e.g. the methanesulphonate, a hydrohalide such as the hydrochloride or an addition compound, such as an addition compound formed with boron trifluoride.

As an example of a chemical means of performing the reduction, there can be used a chiral reducing agent, such as an asymmetric borane derivative, e.g. (+)-B-chlorodiisopino-campheylborane, preferably at a low temperature, e.g. about −10° C. to about −20° C., in an ethereal solvent such as tetrahydrofuran, and preferably in an inert atmosphere.

As will be appreciated by those skilled in the art, an (S)-enantiomer of a compound of formula X can be prepared in a similar manner but using (−)-B-chlorodiisopinocampheylborane instead of the (+)-B-chlorodiisopinocampheylborane.

As an example of biochemical means of performing the reduction, there can be used a culture of a microorganism, more especially a culture of *Hansenulla polymorpha*, a sample of which is deposited under the reference number NCYC 1456 (National Collection of Yeast Culture, Colney Lane, Norwich, Norfolk NR4 7UA, U.K.).

Other microorganisms which may effect the desired stereoselective reduction may be identified by small scale tests with detection of the desired compound of formula (X) by high performance liquid chromatography (HPLC) or other suitable means.

Compounds of formula XI and their salts may be prepared from 4-hydroxybutyl 3-pyridyl ketone, by reaction with thioacetic acid, diethyl azodicarboxylate and triphenyl phosphine or, preferably, by reaction with an arylsulphonyl halide or an alkylsulphonyl halide, e.g. toluene-p-sulphonyl chloride or methanesulphonyl chloride, in the presence of a tertiary base such as triethylamine, N,N-diisopropylethylamine or 1,8-diazabicyclo-[5.4.0]undec-7-ene, followed by reaction with thioacetic acid or an alkali metal salt thereof, e.g. potassium thioacetate, followed, if necessary, by formation of the desired salt by known methods, e.g. by reaction with the appropriate acid, e.g. an arylsulphonic or alkylsulphonic acid, e.g. methanesulphonic acid.

4-Hydroxybutyl 3-pyridyl ketone can be prepared by the reaction of an alkyl nicotinate of the general formula XIII, hereinafter depicted, wherein $R^4$ represents a lower alkyl, e.g. methyl or ethyl, group, with delta-valerolactone in the presence of a base, such as an alkali metal alkoxide, e.g. potassium tert-butoxide, preferably in an ethereal solvent, such as diethyl ether, tert-butyl methyl ether or tetrahydrofuran, or by the reaction of a 3-pyridyl halide, e.g. 3-pyridyl bromide, with a base, e.g. butyl-lithium followed by reaction with delta-valerolactone.

The following Examples illustrate the invention.

Nuclear magnetic resonance (NMR) spectra are recorded at 200 MHz or 400 MHz. Chemical shifts are expressed in ppm relative to tetramethylsilane. Abbreviations have the usual significances, e.g.: s=singlet, d=doublet, t=triplet, m=multiplet, dd=doublet of doublets, dt=triplet of doublets.

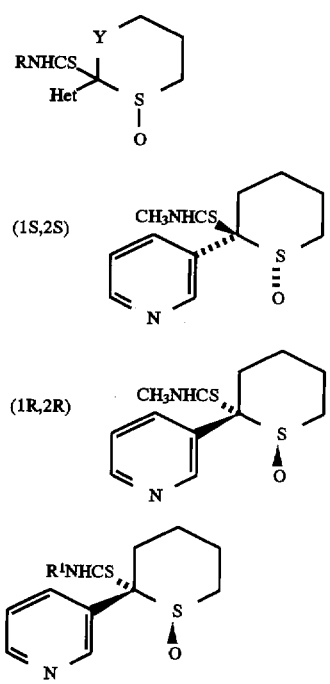

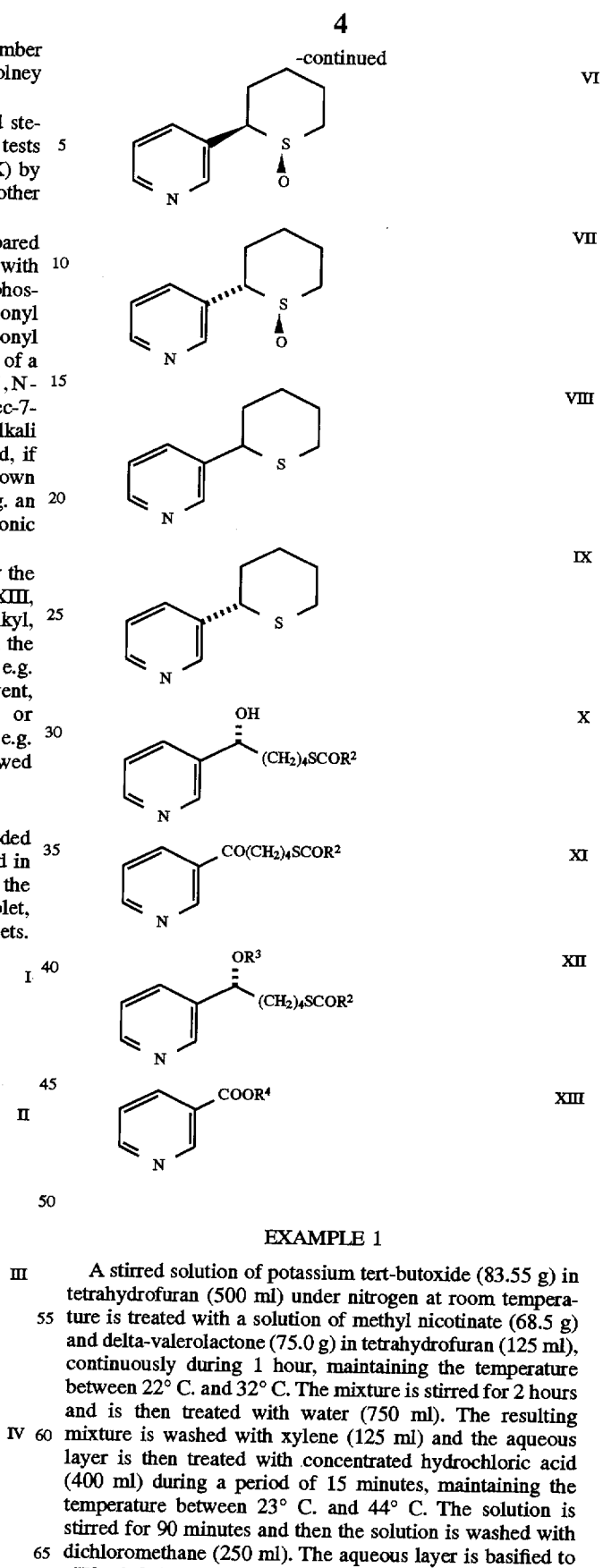

EXAMPLE 1

A stirred solution of potassium tert-butoxide (83.55 g) in tetrahydrofuran (500 ml) under nitrogen at room temperature is treated with a solution of methyl nicotinate (68.5 g) and delta-valerolactone (75.0 g) in tetrahydrofuran (125 ml), continuously during 1 hour, maintaining the temperature between 22° C. and 32° C. The mixture is stirred for 2 hours and is then treated with water (750 ml). The resulting mixture is washed with xylene (125 ml) and the aqueous layer is then treated with concentrated hydrochloric acid (400 ml) during a period of 15 minutes, maintaining the temperature between 23° C. and 44° C. The solution is stirred for 90 minutes and then the solution is washed with dichloromethane (250 ml). The aqueous layer is basified to pH8–pH9 by treatment with aqueous sodium hydroxide solution (specific gravity 1.3; 480 ml) and then it is washed with xylene* (125 ml) and extracted with dichloromethane (3×250 ml). The combined dichloromethane extracts are dried over magnesium sulphate and the solvent is removed by evaporation under reduced pressure, to give 4-hydroxybutyl 3-pyridyl ketone (49.1 g), in the form of a yellow oil which crystallises to form a pale brown solid, m.p. 36°–38° C. [NMR (CDCl$_3$): 1.7(m,2H), 1.9(m,2H), 3.1(t,2H); 3.7(t,2H), 7.4(m,1H), 8.2(dt,1H), 8.8(m,1H), 9.2 (m,1H)].

*This xylene solution is extracted with water (3×100 ml). The aqueous extracts are combined, saturated with sodium chloride and extracted with dichloromethane (3×50 ml). The combined dichloromethane layers are dried over magnesium sulphate and the solvent is removed by evaporation under reduced pressure, to give a further quantity of the same product (14.0 g).

EXAMPLE 2

A solution of 4-hydroxybutyl 3-pyridyl ketone (66.4 g) in tetrahydrofuran (664 ml) under nitrogen at room temperature is treated with methane-sulphonyl chloride (31.6 ml). The mixture is then cooled to 0° C. and treated with N,N-diisopropylethylamine (155 ml), continuously, during 30 minutes, maintaining the temperature below 5° C., and it is stirred for a further period of 10 minutes. The mixture is warmed to 20° C. and is then treated with thioacetic acid during 10 minutes, maintaining the temperature at below 25° C. The mixture is stirred for 2 hours at 35° C. and is then cooled to 20° C. and treated with water (660 ml). The mixture is extracted twice with t-butyl methyl ether (660 ml and 300 ml). The combined extracts are washed with water (2×1300 ml), dried over magnesium sulphate, then treated with decolourising charcoal (8.7 g) and the mixture is stirred for 10 minutes. After filtration, the solvent is removed by evaporation under reduced pressure, to give S-(4-nicotinoylbutyl) thioacetate (80.7 g) in the form of an oil. This oil is dissolved in t-butyl methyl ether (1200 ml) and the solution is treated with methanesulphonic acid (22.1 ml), dropwise, with stirring, then it is stirred for 1 hour and then cooled to 0° C. for 1 hour. The mixture is filtered and the resulting yellow solid is dried with suction at room temperature, to give 3-(5-acetylmercaptopentanoyl) pyridinium methanesulphonate (91.4 g), m.p. 103°–105° C. [NMR (DMSO-d$_6$): 1.6(m,2H), 1.7(m,2H), 2.3(s,3H), 2.4(s, 3H), 2.9(t,2H), 3.2(t,2H), 7.9(dd,1H), 8.7(dt,1H), 9.0(dd, 1H), 9.3(d,1H)].

EXAMPLE 3

A slurry of 3-(5-acetylmercaptopentanoyl)pyridinium methanesulphonate (7.0 g) in ethyl acetate (50 ml) is stirred with a solution of sodium bicarbonate (5 g) in water (50 ml). The ethyl acetate phase is then washed 3 times with water until its pH is 5, dried over magnesium sulphate, filtered and evaporated under reduced pressure to give S-(4-nicotinoylbutyl) thioacetate (4.3 g) in the form of a dark oil which solidifies upon standing (m.p. 43° C.).

A solution of (+)-B-chlorodiisopinocampheylborane (12 g) in dry tetrahydrofuran (20 ml) under a nitrogen atmosphere is cooled to −20° C. and treated with a solution of S-(4-nicotinoylbutyl) thioacetate (4 g) in tetrahydrofuran (10 ml), using a syringe. The reaction mixture is stirred under nitrogen at −20° C. for 20 hours, and then it is treated with diethyl ether (50 ml), followed by diethanolamine (6 g). The mixture is stirred for 4 hours at 20° C., during which time a white precipitate forms. This precipitate is filtered off and washed with heptane (2×5 ml). The combined ethereal and heptane filtrates are evaporated under reduced pressure, to give a light yellow oil (10 g). This oil is chromatographed on silica gel (300 g), eluting with a mixture of ethyl acetate and heptane (700 ml; 1:4 v/v), followed by a mixture of ethyl acetate, isopropanol and 0.880 ammonium hydroxide (700 ml; 84:15:1 v/v), to give (R)-5-hydroxy-5-(3-pyridyl)pentyl thioacetate (3.0 g; 94% ee) in the form of a light yellow oil. [NMR (CDCl$_3$): 8.5(s,1H), 8.45(d,1H), 7.7(d,1H), 7.3(dd, 1H), 4.7(t,1H), 3.1(s,1H), 2.85(t,2H), 2.3(s,3H), 1.9–1.0(m, 6H). Elemental analysis: C,62.2; H,7.9; N,4.7; S,11.2%; calculated: C,60.2; H,7.2; N,5.8; S,13.3%. (Sample contains 2 to 3% pinene)].

The percentage enantiomeric excess (% ee) is determined by chiral HPLC, using the following conditions: Chiralcel OD 25 cm×4.5 mm column; mobile phase of isopropanol/heptane (15:85 v/v); flow rate 1.0 ml/min.; UV detection 270 nm.

EXAMPLE 4

A solution of (R)-5-hydroxy-5-(3-pyridyl)pentyl thioacetate (2.8 g) in dry dichloro- methane (15 ml) under a nitrogen atmosphere is cooled to −15° C. and treated with triethylamine (1.4 g) using a syringe. It is then treated with methanesulphonyl chloride (1.5 g) by syringe during 5 minutes. The temperature rises spontaneously to −8° C. during this addition. When the addition is complete the reaction mixture is allowed to warm to room temperature. After 2 hours it is washed with water (4×15 ml) until its pH is 7. The organic phase is then dried with magnesium sulphate, filtered and evaporated under reduced pressure, to give (R)-5-methanesulphonyloxy-5-(3-pyridyl)pentyl thioacetate (3.66 g), in the form of a yellow oil. This material is used in the next step without further purification.

EXAMPLE 5

A solution of (R)-5-methanesulphonyloxy-5-(3-pyridyl) pentyl thioacetate (3.66 g; prepared as described in Example 4) in dry methanol (15 ml) at 20° C. under a nitrogen atmosphere is treated with a solution of sodium methoxide (30% w/v; 2.1 ml). After 1 hour it is diluted with ethyl acetate (30 ml) and washed with saturated brine (2×15 ml). The organic phase is then dried with magnesium sulphate, filtered and evaporated under reduced pressure, to give a yellow oil (2.3 g). This oil is chromatographed on silica gel (100 g), using as eluent a mixture of ethyl acetate and heptane (1:4 v/v), to give (S)-2-(3-pyridyl)tetrahydro-2H-thiopyran (1.8 g; 94% ee) in the form of a white solid, m.p. 52° C. Recrystallisation of this material from pentane gives 0.9 g of white solid of 94% ee. [NMR (CDCl$_3$): 8.6(s,1H), 8.5(d,1H), 7.7(d,1H), 7.25(dd,1H), 3.9(d,1H), 2.9(t,1H), 2.7 (d,1H), 2.2–1.2(m,6H). Elemental analysis: C,66.6; H,7.5; N,7.7; S,18.4%; calculated: C,66.9; H,7.3; N,7.8; S,17.88%.

The % ee is determined by chiral HPLC, using the following conditions: Chiralcel OD 25 cm×4.5 mm column; mobile phase of isopropanol/heptane (15:85 v/v); flow rate 0.5 ml/min; UV detection 270 nm.

EXAMPLE 6

A solution of (S)-2-(3-pyridyl)tetrahydro-2H-thiopyran (0.6 g) and copper (II) acetylacetonate (0.8 g) in ethanol (15 ml) is treated with hydrogen peroxide (2 ml; 27.5%), in 0.5 ml portions during a 20 hour period. Two hours after the final addition the reaction mixture is diluted with ethyl acetate (30 ml) and washed with saturated brine (2×30 ml). The combined brine washes are then extracted with ethyl acetate (3×30 ml), the combined ethyl acetate phases are dried over magnesium sulphate, filtered and evaporated under reduced pressure, to give (1R,2S)-2-(3-pyridyl) tetrahydro-2H-thiopyran 1-oxide (0.5 g), in the form of a white solid, m.p. 131° C. [NMR (CDCl$_3$): 8.7(s,2H), 7.7(d, 1H); 7.3(s,1H); 3.6(dd,2H); 2.8(t,1H); 2.3–1.5(m,6H). Elemental analysis: C,61.3; H,6.7; N,6.9; S,16.5.%; calculated: C,61.5; H,6.7; N,7.1; S,16.4%.]

The % ee is determined by chiral HPLC, using the following conditions: Chiralcel OD 25 cm×4.5 mm column; mobile phase of heptane/methanol/isopropanol (93:5:2 v/v); flow rate 1.5 ml/min; UV detection 270 nm.

EXAMPLE 7

Ammonia gas is condensed at −50° C. to obtain 2 ml of liquid ammonia, which is treated with iron (III) nitrate (0.0015 g), followed by sodium metal (0.02 g). The solution turns blue and then dark grey after 20 minutes. It is then treated with a solution of (1R,2S)-2-(3-pyridyl)tetrahydro-2H-thiopyran 1-oxide (0.06 g) in tetrahydrofuran (8 ml) during 2 minutes, at −40° C. The mixture is stirred for 2 minutes and is then treated with a solution of methyl isothiocyanate (0.033 g) in tetrahydrofuran (2 ml), by syringe. The reaction mixture is stirred for 5 minutes at −35° C. and then treated with ammonium chloride (0.05 g) and warmed to 20° C. The mixture is treated with methanol (0.3 ml) and evaporated under reduced pressure. The residue is partitioned between brine (10 ml) and dichloromethane (3×30 ml). The organic phases are combined and dried with magnesium sulphate, filtered and evaporated under reduced pressure, to give (1R,2R)-2-(3-pyridyl)-N-methyltetrahydro-2H-thiopyran-2-carbothioamide 1-oxide (0.4 g; 99% ee) in the form of a white solid, m.p. 215° C. [NMR (CDCl$_3$): 8.7(s,1H); 8.5(s,2H); 8.1(d,1H); 7.3(s,1H); 3.8(s,1H); 3.1(d,3H); 2.8(s,1H); 2.4–1.5(m,6H)].

The % ee is determined by chiral HPLC, using the following conditions: Chiralcel OD 25 cm×4.5 mm column; mobile phase of heptane/methanol/isopropanol (93:5:2 v/v); flow rate 1.5 ml/min; UV detection 270 nm.

EXAMPLE 8

A solution of potassium tert-butoxide (83.55 g) in tetrahydrofuran (500 ml) at 22° C. is treated, dropwise, with a solution of methyl nicotinate (68.5 g) and delta-valerolactone (75.0 g) in tetrahydrofuran (125 ml) during a period of 1 hour. The solution is then stirred at 23° C. for 2 hours. The reaction mixture is diluted with water and washed with toluene (125 ml). The organic phase is discarded and the aqueous phase is treated dropwise with concentrated hydrochloric acid (400 ml; 37% w/v). The solution is stirred for a further 2 hours. The solution is then washed with dichloromethane (250 ml). The organic phase is discarded and the aqueous phase is treated with aqueous sodium hydroxide solution to bring it to between pH8 and pH9. The aqueous phase is then washed with toluene (125 ml) and the organic phase is back washed with water (3×100 ml). The two aqueous phases are combined and extracted with dichloro- methane. The dichloromethane extract is dried over magnesium sulphate, and evaporated to dryness, to give 4-hydroxybutyl 3-pyridyl ketone (61.1 g) in the form of an oil which crystallises to form a pale brown solid, m.p. 36°–38° C. [NMR (CDCl$_3$): 1.7(m,2H), 1.9(m,2H), 3.1(t, 2H), 3.7(t,2H), 7.4(m,1H), 8.2(dt,1H), 8.8(m, 1H), 9.2(m, 1H)].

EXAMPLE 9

A solution of 4-hydroxybutyl 3-pyridyl ketone (89.6 g) in tetrahydrofuran (750 ml) under nitrogen at room temperature is treated with N,N-diisopropylethylamine (155.1 g). The mixture is then cooled to 0° C. and treated with methanesulphonyl chloride (63.0 g) continually during 10 minutes, maintaining the temperature at between 5° C. and 10° C., and then the mixture is stirred for 10 minutes. It is then treated with thioacetic acid (45.7 g) during 10 minutes and allowed to warm to 35° C. It is stirred for 1 hour at 35° C. and then cooled to 20° C. It is then treated with water (750 ml) during 5 minutes and the mixture is extracted twice with toluene (750 ml and 350 ml). The combined extracts are washed with water and evaporated, to give S-(4-nicotinoylbutyl) thioacetate (113.4 g), in the form of an oil.

This oil is treated with tert-butyl methyl ether, followed by decolourising charcoal and, after filtration, treated with methanesulphonic acid (48.1 g), dropwise. The mixture is cooled to 0° C. and filtered and the resulting solid is dried with suction at room temperature, to give 3-(5-acetylmercapto-pentanoyl)pyridinium methanesulphonate (139.4 g) in the form of a yellow/orange solid, m.p. 103°–105° C. [NMR (DMSO-d$_6$): 1.6(m,2H), 1.7(m,2H), 2.3(s,3H), 2.4(s,3H), 2.9(t,2H), 3.2(t,2H), 7.9(dd,1H), 8.7 (dt,1H), 9.0(dd,1H), 9.3(d,1H)].

EXAMPLE 10

A solution of S-(4-nicotinoylbutyl) thioacetate (1.0 g) in dry dichloromethane (10 ml) containing 4A molecular sieves, under nitrogen, is treated with boron trifluoride trietherate (0.5 ml) and the mixture is cooled to 0° C. and stirred for one hour. The reaction mixture is then cooled to −20° C. and treated with a solution of (+)-B-chloro-diisopinocampheylborane (2.0 g) in dichloromethane (10 ml) and stirred at between −15° and −20° C. for 20 hours. It is then allowed to warm to room temperature and treated with acetaldehyde (0.3 ml) and stirred for 5 hours. It is cooled to 10° C., treated with aqueous sodium hydroxide solution (15 ml; 3.05N) and stirred for 2 minutes. The organic phase is separated, washed with water (20 ml), cooled to 10° C. and extracted with dilute hydrochloric acid (2×15 ml; 1N) and washed with water (2×15 ml) until its pH is 7. These washings are combined with the acid extracts, washed with tert-butyl methyl ether (2×50 ml), cooled to 5° C., treated dropwise with aqueous sodium hydroxide solution (9N) until the pH is 10 and extracted with tert-butyl methyl ether (2×50 ml). These organic extracts are combined, washed with water (2×15 ml) until the pH is 7, dried over magnesium sulphate and evaporated, to give (R)-5-hydroxy-5-(3-pyridyl)pentyl thioacetate (0.76 g; 94% ee) in the form of a yellow oil.

EXAMPLE 11

A solution of (R)-5-hydroxy-5-(3-pyridyl)pentyl thioacetate (10.0 g) in dichloromethane (200 ml) under nitrogen is cooled to 0° C. and treated with triethylamine (7 ml), followed by methanesulphonyl chloride (3.8 ml), dropwise between −5° C. and 0° C., during 5 minutes. The reaction mixture is then warmed to room temperature. After 60 minutes the mixture is cooled to 10° C. and treated, dropwise during 10 minutes, with a solution of sodium methoxide in methanol (20 ml; 25% w/v). The mixture is allowed to warm to room temperature. After 30 minutes the mixture is washed with water until the pH is between 9 and 10, dried over magnesium sulphate, evaporated and chromatographed, to give (S)-2-(3-pyridyl)tetrahydro-2H-thiopyran (7.5 g; 91% ee), in the form of an amber oil.

EXAMPLE 12

A solution of (S)-2-(3-pyridyl)tetrahydro-2H-thiopyran (1.5 g) in dichloromethane (15 ml) is treated with ethanol (15 ml), followed by copper acetylacetonate (0.22 g). The green-blue solution is treated with a solution of hydrogen peroxide (2 ml; 27.5%) in ethanol (2 ml). After 2 hours the solution is treated with a further quantity of solution of hydrogen peroxide (1 ml; 27.5%) in ethanol (1 ml), followed by a similar further quantity each hour for seven hours. Thus, a total of 10 ml of 27.5% hydrogen peroxide is used. After a further period of four hours, the mixture is treated with dichloromethane (10 ml) and extracted with water (4×25 ml). The combined aqueous extract is treated with sodium ethylenediaminetetraacetate (0.5 g), followed by sufficient solid sodium chloride to form a saturated solution. This is then extracted with dichloromethane (4×50 ml), and the combined organic extract is dried over magnesium sulphate and evaporated, to give (1R,2S)-2-(3-pyridyl) tetrahydro-2H-thiopyran 1-oxide (1.1 g), in the form of a yellow solid.

EXAMPLE 13

*Hansenulla polymorpha* is cultivated in a 100 ml Erlenmeyer flask containing 30 ml of yeast malt nutrient medium (Difco) at a concentration of 21 g/l. After 40 hours, the culture is treated with S-(4-nicotinoylbutyl) thioacetate (30mg), and shaken for 29 hours. The reaction mixture is then extracted with ethyl acetate and the extract is dried over sodium sulphate and evaporated. The resulting residue is dissolved in a mixture of heptane and isopropanol (90:10 v/v) and this solution is examined by chiral HPLC using a column of Chiralcel OD, an injection volume of 5 μl, a flow rate of 1 ml/minute, a mobile phase of a mixture of heptane and isopropanol (90:10 v/v) , and UV detection at 230 nm. It is found that the conversion factor is 47%, the yield of (R)-5-hydroxy-5-(3-pyridyl)pentyl thioacetate is 22% and the enantiomeric excess is greater than 95%. The activity of the culture [number of mg of (R)-5-hydroxy-5-(3-pyridyl) pentyl thioacetate produced per hour and per liter of culture] is 11mg/hr.l. The structure of the product is confirmed by its NMR spectrum.

EXAMPLE 14

A solution of potassium tert-butoxide (82.14 g) and methyl nicotinate (68.5 g) in tetrahydrofuran (500 ml) is stirred under an atmosphere of nitrogen at 45° C. to 50° C. It is then treated with a solution of delta-valerolactone (75.0 g) in tetrahydrofuran (125 ml) during 2 hours, forming a suspension, which is stirred for 2 hours at 45°–50° C. It is then treated with water (400 ml), followed by concentrated hydrochloric acid (177.0 g) during 15 minutes. The reaction mixture is stirred for 75 minutes at 45°–50° C., then cooled to 20° C. and washed with toluene (2×250 ml). The aqueous layer is basified to pH7.5 by treatment with aqueous sodium hydroxide solution, and is then left standing overnight at ambient temperature, after which the mixture is extracted with toluene (250 ml). Sodium chloride (120 g) is dissolved in the aqueous layer which is then extracted with dichloromethane (4×250 ml). The combined dichloromethane extracts are dried over magnesium sulphate and filtered. This dichloromethane solution is stirred under nitrogen and treated with N,N-diisopropyl-ethylamine (105 ml). The stirred solution is cooled to 0° C. and then treated with methanesulphonyl chloride (42.6 ml), dropwise, keeping the temperature below 10° C. The mixture is washed with water (50 ml), dried over magnesium sulphate and filtered. The filtrate is stirred and cooled in an ice-bath. It is then treated with methanesulphonic acid (32.5 ml) during 5 minutes, the mixture is stirred for 10 minutes, then treated with tert-butyl methyl ether (150 ml), dropwise during 20 minutes. The resulting suspension is stirred, with cooling in an ice-bath, until crystallisation is complete, to give 3-(5-methanesulphonyl-pentanoyl)pyrdinium methanesulphonate (112.1 g), in the form of a white powder, m.p. 74° C.

We claim:

1. A process for the preparation of a compound of formula (IX)

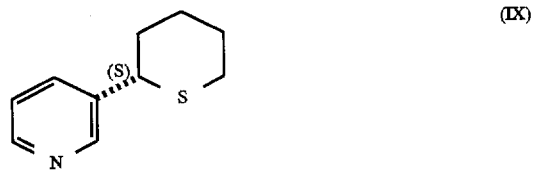

which comprises the following step sequence:

a) reducing a compound of formula (XI)

CO(CH$_2$)$_4$SCOR$^2$ wherein R$^2$ is a straight or branched C$_{1-4}$ alkyl group or a salt or addition compound thereof using a chiral reducing agent or by biochemical reducing means to provide a compound of formula (X)

OH (R) (CH$_2$)$_4$SCOR$^2$ wherein R$^2$ is as defined previously;

b) converting a compound of formula (X) to a compound of formula (XII)

OR$^3$ (R) (CH$_2$)$_4$SCOR$^2$ wherein R$^2$ is as defined previously and R$^3$ represents an alkyl- or arylsulphonyl group; and c) cyclising the so-formed (R) isomer of formula (XII) to provide the desired (S) isomer of formula (IX).

2. A process for the preparation of a compound of formula (IX)

(S) S N which comprises cyclising a compound of formula (XII)

OR$^3$ (R) (CH$_2$)$_4$SCOR$^2$ wherein R$^2$ represents a straight or branched C$_{1-4}$ alkyl group and R$^3$ is an alkyl or arylsulphonyl group.

3. A process for the preparation of a compound of formula (X)

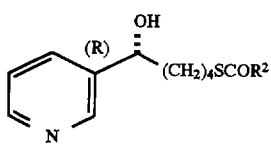

wherein $R^2$ represents a straight or branched $C_{1-4}$ alkyl group, which comprises reducing a compound of formula (XI)

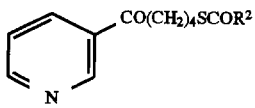

wherein $R^2$ is as defined previously, or a salt or addition compound thereof using a chiral reducing agent or by biochemical reducing means.

4. A process as claimed in claim 1 wherein a compound of formula (XII) is cyclised by treatment with a nucleophilic base.

5. A process as claimed in claim 4 wherein the nucleophilic base is an alkali metal alkoxide and the reaction is effected in an alkanol solvent.

6. A process as claimed in claim 1 wherein the reduction to provide a compound of formula (X) is effected chemically using an asymmetric borane derivative.

7. A process as claimed in claim 6 wherein the reduction is effected at a temperature of about $-10°$ C. to about $-20°$ C.

8. A process as claimed in claim 1 wherein the reduction to provide a compound of formula (X) is effected biochemically using a culture of the microorganism *Hansenulla Polymorpha*.

9. A compound of formula (X)

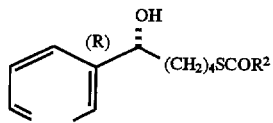

wherein $R^2$ is a straight or branched $C_{1-4}$ alkyl group, and salts thereof.

10. A compound of formula (XII)

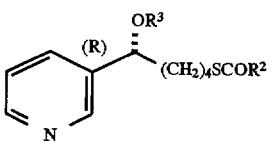

wherein $R^2$ is a straight or branched $C_{1-4}$ alkyl group and $R^3$ is alkyl-or arylsulphonyl, and salts thereof.

11. A process as claimed in claim 3 wherein the reduction to provide a compound of formula (X) is effected biochemically using a culture of the microorganism *Hansenulla Polymorpha*.

* * * * *